US011819328B2

(12) United States Patent
Mantri et al.

(10) Patent No.: US 11,819,328 B2
(45) Date of Patent: *Nov. 21, 2023

(54) METHODS AND SYSTEMS FOR ENDOBRONCHIAL DIAGNOSTICS

(71) Applicant: Pulmonx Corporation, Redwood City, CA (US)

(72) Inventors: Surag Mantri, Sunnyvale, CA (US); Srikanth Radhakrishnan, Cupertino, CA (US)

(73) Assignee: Pulmonx Corporation, Redwood City, CA (US)

( * ) Notice: Subject to any disclaimer, the term of this patent is extended or adjusted under 35 U.S.C. 154(b) by 218 days.

This patent is subject to a terminal disclaimer.

(21) Appl. No.: 17/163,173

(22) Filed: Jan. 29, 2021

(65) Prior Publication Data

US 2021/0177321 A1 Jun. 17, 2021

Related U.S. Application Data

(60) Continuation of application No. 16/107,849, filed on Aug. 21, 2018, now Pat. No. 10,932,706, which is a
(Continued)

(51) Int. Cl.
A61B 5/1455 (2006.01)
A61B 5/08 (2006.01)
(Continued)

(52) U.S. Cl.
CPC ...... *A61B 5/14552* (2013.01); *A61B 1/00082* (2013.01); *A61B 1/2676* (2013.01);
(Continued)

(58) Field of Classification Search
CPC ..... A61B 5/14552; A61B 5/1459; A61B 5/08; A61B 5/085; A61B 5/091; A61B 5/6853; A61M 16/0003; A61M 16/04–0409
See application file for complete search history.

(56) References Cited

U.S. PATENT DOCUMENTS 7,798,147 B2 9/2010 Hendricksen et al.
7,883,471 B2 2/2011 Aljuri et al.
(Continued)

FOREIGN PATENT DOCUMENTS

WO WO-2009135070 A1 11/2009

OTHER PUBLICATIONS

Casanova et al. Inspiratory-to-total lung capacity ratio predicts mortality in patients with chronic obstructive pulmonary disease. Am J Respir Crit Care Med, vol. 171, pp. 591-597 (2005).
(Continued)

*Primary Examiner* — Thaddeus B Cox
(74) *Attorney, Agent, or Firm* — Kilpatrick Townsend & Stockton LLP

(57) ABSTRACT

Methods and systems for targeting, accessing and diagnosing diseased lung compartments are disclosed. The method comprises introducing a diagnostic catheter with an occluding member at its distal end into a lung segment via an assisted ventilation device; inflating the occluding member to isolate the lung segment; and performing a diagnostic procedure with the catheter while the patient is ventilated. The proximal end of the diagnostic catheter is configured to be attached to a console. The method may also comprise introducing the diagnostic catheter into the lung segment; inflating the occluding member to isolate the lung segment; and monitoring blood oxygen saturation. The method may further comprise introducing the diagnostic catheter into the lung segment; determining tidal flow volume in the lung segment; determining total lung capacity of the patient; and determining a flow rank value based on the tidal flow volume of the lung segment and the total lung capacity.

5 Claims, 9 Drawing Sheets

Related U.S. Application Data division of application No. 14/339,197, filed on Jul. 23, 2014, now Pat. No. 10,076,271, which is a division of application No. 13/174,633, filed on Jun. 30, 2011, now Pat. No. 8,808,194.

(60) Provisional application No. 61/360,811, filed on Jul. 1, 2010.

(51) Int. Cl.

| | | |
|---|---|---|
| *A61M 16/04* | (2006.01) | |
| *A61B 5/085* | (2006.01) | |
| *A61B 5/091* | (2006.01) | |
| *A61B 1/00* | (2006.01) | |
| *A61B 1/267* | (2006.01) | |
| *A61B 5/087* | (2006.01) | |
| *A61B 5/145* | (2006.01) | |
| *A61B 5/00* | (2006.01) | |
| *A61M 16/00* | (2006.01) | |
| *A61M 16/10* | (2006.01) | |

(52) U.S. Cl.
CPC ............... *A61B 5/08* (2013.01); *A61B 5/085* (2013.01); *A61B 5/087* (2013.01); *A61B 5/091* (2013.01); *A61B 5/14542* (2013.01); *A61B 5/6853* (2013.01); *A61M 16/0003* (2014.02); *A61M 16/0404* (2014.02); *A61M 2016/0036* (2013.01); *A61M 2016/102* (2013.01); *A61M 2230/205* (2013.01); *A61M 2230/43* (2013.01)

(56) References Cited

U.S. PATENT DOCUMENTS

| | | | |
|---|---|---|---|
| 8,136,526 B2 | 3/2012 | Perkins et al. | |
| 8,808,194 B2 | 8/2014 | Mantri et al. | |
| 10,076,271 B2 | 9/2018 | Mantri et al. | |
| 10,932,706 B2 | 3/2021 | Mantri et al. | |
| 2002/0165462 A1* | 11/2002 | Westbrook | A61B 5/7275 |
| | | | 600/529 |
| 2003/0051733 A1 | 3/2003 | Kotmel et al. | |
| 2006/0264772 A1 | 11/2006 | Aljuri et al. | |
| 2007/0060811 A1* | 3/2007 | Roberts | A61B 5/1459 |
| | | | 600/339 |
| 2007/0142742 A1 | 6/2007 | Aljuri et al. | |
| 2008/0027343 A1 | 1/2008 | Fields et al. | |
| 2008/0188733 A1* | 8/2008 | Al-Ali | A61B 5/6843 |
| | | | 600/509 |
| 2009/0209839 A1* | 8/2009 | Ochs | A61B 5/742 |
| | | | 600/364 |
| 2010/0113904 A1* | 5/2010 | Batchelder | A61B 5/14552 |
| | | | 600/324 |
| 2010/0158795 A1 | 6/2010 | Aljuri et al. | |

OTHER PUBLICATIONS

Notice of allowance dated Apr. 21, 2014 for U.S. Appl. No. 13/174,633.
Office action dated Jul. 2, 2020 for U.S. Appl. No. 16/107,849.
Office action dated Oct. 22, 2013 for U.S. Appl. No. 13/174,633.
U.S. Appl. No. 14/339,197 Notice of Allowance dated May 21, 2018.
U.S. Appl. No. 14/339,197 Office Action dated Oct. 12, 2017.
U.S. Appl. No. 16/107,849 Notice of Allowance dated Nov. 2, 2020.
Wang, et al. Perfusion scintigraphy in the evaluation for lung volume reduction surgery: correlation with clinical outcome. Radiology. Oct. 1997;205(1):243-8.

* cited by examiner

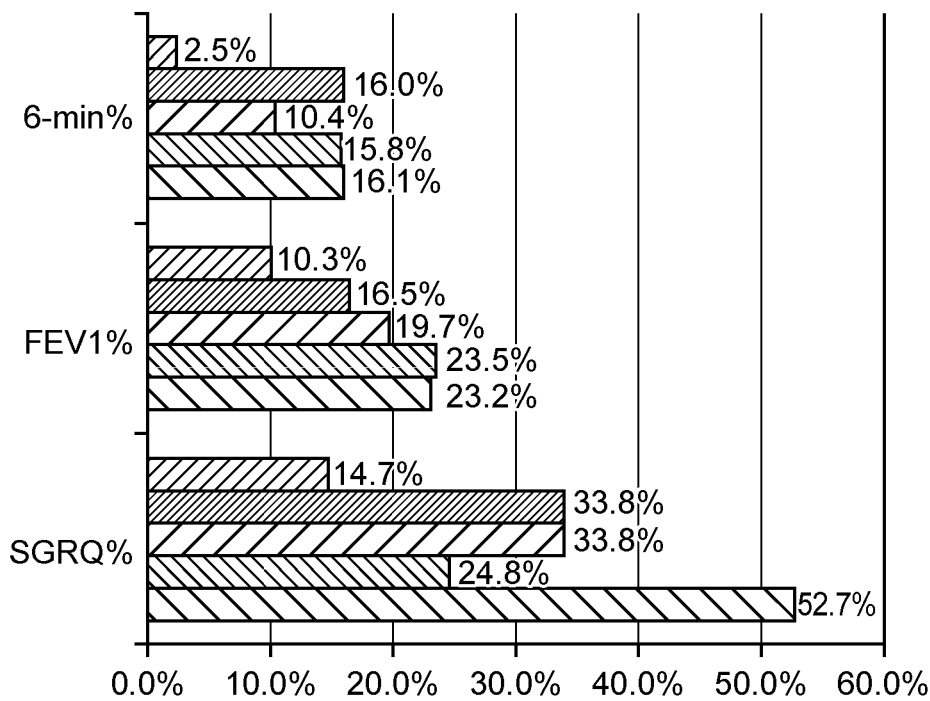
FIG. 10
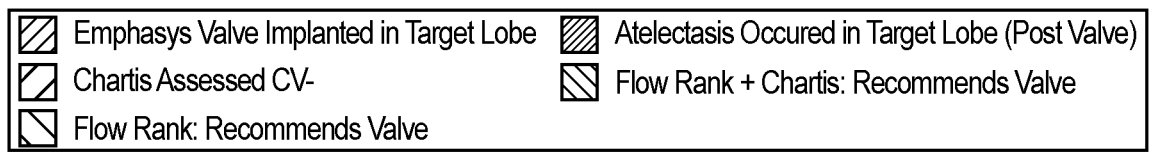
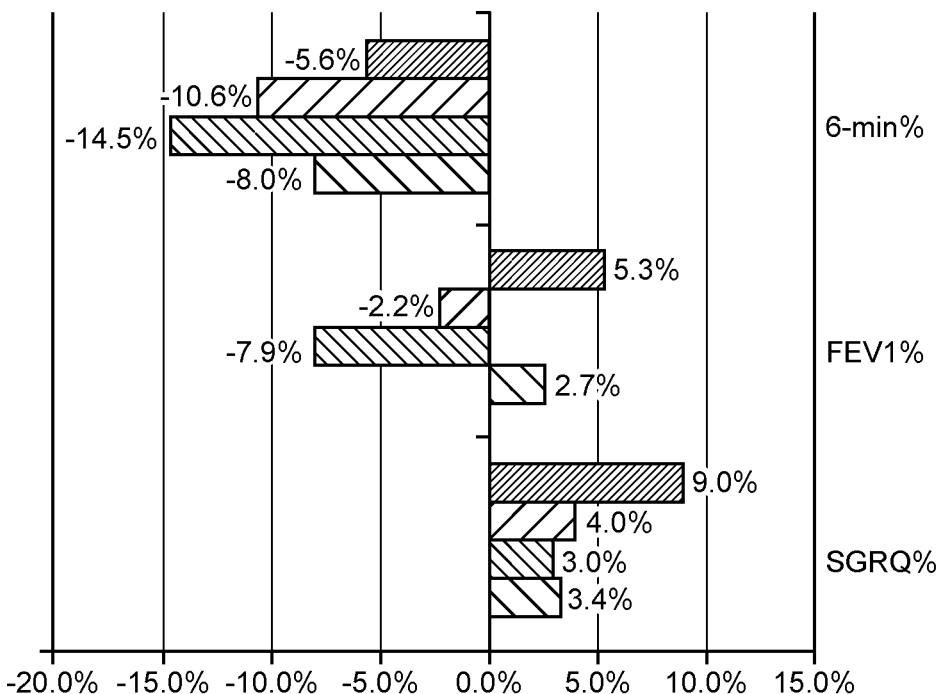
FIG. 11

METHODS AND SYSTEMS FOR ENDOBRONCHIAL DIAGNOSTICS

CROSS-REFERENCE TO RELATED APPLICATION

The present application is a continuation of U.S. patent application Ser. No. 16/107,849, filed Aug. 21, 2018, now U.S. Pat. No. 10,932,706, which is a divisional of U.S. patent application Ser. No. 14/339,197, filed Jul. 23, 2014, now U.S. Pat. No. 10,076,271, which is a divisional of U.S. patent application Ser. No. 13/174,633, filed Jun. 30, 2011, now U.S. Pat. No. 8,808,194, which claims priority under 35 U.S.C. Section 119(e) to U.S. Provisional Patent Application Ser. No. 61/360,811, filed Jul. 1, 2010, the full disclosures of which are hereby incorporated by reference.

BACKGROUND OF THE INVENTION

1. Field of the Invention

This invention relates generally to methods for diagnosis and treatment of lung disease.

2. Description of the Related Art

Chronic obstructive pulmonary disease (COPD), including emphysema and chronic bronchitis, is a significant medical problem currently affecting around 16 million people in the U.S. alone (about 6% of the U.S. population). In general, two types of diagnostic tests are performed on a patient to determine the extent and severity of COPD: 1) imaging tests; and 2) functional tests. Imaging tests, such as chest x-rays, computerized tomography (CT) scans, Magnetic Resonance Imaging (MRI) images, perfusion scans, and bronchograms, provide a good indicator of the location, homogeneity and progression of the diseased tissue. However, imaging tests do not provide a direct indication of how the disease is affecting the patient's overall lung function and respiration. Lung function can be better assessed using functional testing, such as spirometry, plethysmography, oxygen saturation, and oxygen consumption stress testing, among others. Together, these imaging and functional diagnostic tests are used to determine the course of treatment for the patient.

One of the emerging treatments for COPD involves the endoscopic introduction of endobronchial occluders or one-way valve devices ("endobronchial valves" or "EBVs") into pulmonary passageways to reduce the volume of one or more hyperinflated lung compartments, thus allowing healthier compartments more room to breathe and perhaps reducing pressure on the heart. Examples of such a method and implant are described, for example, in U.S. patent application Ser. No. 11/682,986 and U.S. Pat. No. 7,798,147, the full disclosures of which are hereby incorporated by reference. One-way valves implanted in airways leading to a lung compartment restrict air flow in the inhalation direction and allow air to flow out of the lung compartment upon exhalation, thus causing the adjoining lung compartment to collapse over time. Occluders block both inhalation and exhalation, also causing lung collapse over time.

It has been suggested that the use of endobronchial implants for lung volume reduction might be most effective when applied to lung compartments which are not affected by collateral ventilation. Collateral ventilation occurs when air passes from one lung compartment to another through a collateral channel rather than the primary airway channels. If collateral airflow channels are present in a lung compartment, implanting a one-way valve or occluder might not be as effective, because the compartment might continue to fill with air from the collateral source and thus fail to collapse as intended. In many cases, COPD manifests itself in the formation of a large number of collateral channels caused by rupture of alveoli due to hyperinflation, or by destruction and weakening of alveolar tissue.

An endobronchial catheter-based diagnostic system typically used for collateral ventilation measurement is disclosed in U.S. Patent Publication No. 2003/0051733 (hereby incorporated by reference), wherein the catheter uses an occlusion member to isolate a lung segment and the instrumentation is used to gather data such as changes in pressure and volume of inhaled/exhaled air. Current state of the art methods for collateral ventilation measurement are disclosed in U.S. Pat. No. 7,883,471 and U.S. Patent Publication Nos. 2008/0027343 and 2007/0142742 (all of which are hereby incorporated by reference), in which an isolation catheter is used to isolate a target lung compartment and pressure changes therein are sensed to detect the extent of collateral ventilation. The applications also disclose measurement of gas concentrations to determine the efficiency of gas exchange within the lung compartment. Similar methods are disclosed in PCT Application No. WO2009135070A1 (hereby incorporated by reference), wherein gas concentration changes in a catheter-isolated lung portion allow collateral ventilation to be determined.

Quantifying collateral ventilation via collateral resistance measurement and calculations typically takes about two to five minutes. During this time, the physician must ensure the patient is tolerating sedation, manage secretions to prevent occlusion within the catheter lumen, and maintain balloon seal/position within the target airway. Any one of these factors may extend the assessment time and compromise the assessment results. Thus, there is a need to quantify the magnitude of collateral ventilation within a lung compartment (lobe, segment, sub-segment, or the like) more quickly and efficiently.

Another unmet need is a simple and accurate method for determining the perfusion status of a lung segment (i.e., how well a lung segment is being supplied with blood). The current gold standard for determining perfusion status is using ventilation/perfusion scintigraphy (Wang S C et al. Perfusion scintigraphy in the evaluation for lung volume reduction surgery: correlation with clinical outcome. Radiology. 1997 October; 205(1): 243-8). This method requires the use of a gamma camera following the injection of radioactive microspheres. This scanning technique is highly sensitive for detection of regional abnormalities of blood flow and is primarily used for the diagnosis of pulmonary embolism. It has also been tried in lung volume reduction surgery; the goal is to determine what regions of the lung are non-functional based on a mismatch of ventilation and perfusion. Though promising, the accuracy and application of ventilation/perfusion scintigraphy has yet to be proven due to lackluster results in its application to lung volume reduction surgery. Further, the dyes and separate scanning machinery necessary for scintigraphy means that this system is both complicated and costly to use.

It would also be desirable to measure oxygen absorption within the lung, since this could be indicative of the functionality of the lung. Diseased lung portions presumably would not absorb oxygen in the blood stream as well as non-diseased portions. It would thus be desirable to provide a method for assessing and comparing oxygen absorption between the various lung segments.

Yet another unmet need in diagnostics is the determination of how well a target lobe is ventilating. If the target lobe is not ventilating well as compared to other lobes, then a viable treatment option would be to isolate the lobe via Endoscopic Lung Volume Reduction (ELVR) to allow better ventilating lobes to utilize the same space and thereby increase the overall efficiency of the lung. In case the lobe has collateral ventilation (CV positive) and does not ventilate well, the treatment may constitute closing off the lobe using ELVR (e.g., endobronchial valves). ELVR then becomes a method to divert airflow to lobes with better ventilation and perfusion rather than a means to reduce lobe size.

If the target lobe ventilates well, then one may not want to isolate the lobe with valves, even if other disease parameters are present in that lobe. For example, if a lobe does not have collateral ventilation (CV negative) but still ventilates well, one may not want to close off the lobe using ELVR. One measurable parameter that can determine how well a lobe is ventilating is tidal expiratory and/or inspiratory flow. One could also monitor other parameters that may correlate to lobe function including airway resistance and pressures, such as the perfusion efficiency of blood in the capillaries of the alveoli.

There is also a need to determine abnormalities in gas exchange/blood flow to aid with targeting of lobes for endoscopic lung volume reduction in real-time. If the segment/lobe has collateral ventilation, a physician may still want to treat the lobe if the gas exchange is sub-optimal. Ultimately, such a method would enable physicians to treat both heterogeneous and homogeneous patients using EBVs or other pulmonary implants that cause lung collapse.

Therefore, it would be advantageous to have new diagnostic techniques for evaluating the state of lung disease progression, such as determining the presence and degree of collateral ventilation, the viability of lung tissue using parameters such as blood flow and oxygen permeation, as well as ranking a lung portion for severity of disease using a function of the diagnostic parameters. At least some of these objectives will be met by the embodiments described herein.

SUMMARY OF THE INVENTION

This application discloses methods and systems for targeting, accessing and diagnosing diseased lung compartments. In one aspect, a method of determining collateral ventilation in a patient comprises introducing a diagnostic catheter with an occluding member at its distal end into a lung segment via an assisted ventilation device, inflating the occluding member to isolate the lung segment, and performing a diagnostic procedure with the catheter while the patient is ventilated via the assisted ventilation device. The proximal end of the diagnostic catheter is configured to be attached to a console, and data from the diagnostic procedure may be displayed on the console. In one embodiment, the diagnostic procedure comprises determining one or more characteristics of respiration such as flow rate, pressure, or resistance. The characteristics may be used, for example, to determine the presence of collateral ventilation. In one embodiment, the assisted ventilation device may include a ventilation mask.

In another aspect, a method of assessing the functionality of a lung segment in a patient comprises introducing a diagnostic catheter with an occluding member at its distal end into the lung segment, inflating the occluding member to isolate the lung segment, and monitoring blood oxygen saturation of the patient. The proximal end of the diagnostic catheter is configured to be attached to a console, and in some embodiments the method may involve viewing data on the console related to the lung segment being assessed. The monitoring step may comprise monitoring oxygen saturation before and after the inflating step. After the monitoring step, the occluding member may be deflated. Oxygen saturation may be further monitored after deflating the occluding member. Oxygen saturation may be monitored by a pulse oximeter.

In yet another aspect, a method of assessing the functionality of a lung segment of a patient comprises introducing a diagnostic catheter with an occluding member at its distal end into the lung segment, determining tidal flow volume in the lung segment, determining total lung capacity of the patient, and determining a flow rank value based on the tidal flow volume of the lung segment and the total lung capacity. The proximal end of the diagnostic catheter is configured to be attached to a console, and at least the tidal volume and total lung capacity are typically displayed on the console. In one embodiment a treatment option is determined based on the flow rank value. The occluding member may be inflated to isolate the lung segment.

The method may further comprise determining the presence of collateral ventilation in the lung segment and a treatment option may be determined based on the presence of collateral ventilation.

Further aspects and embodiments of the present invention are described in further detail below, in reference to the attached drawings.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 10 is a chart showing results obtained by using the methods shown in FIGS. 8 and 9.

FIG. 11 is a chart showing results obtained by using the methods shown in FIGS. 8 and 9.

DETAILED DESCRIPTION

Although the detailed description contains many specifics, these should not be construed as limiting the scope of the invention but merely as illustrating different examples and aspects of the invention. Various modifications, changes and variations may be made in the disclosed embodiments without departing from the spirit and scope of the invention.

The present application provides methods and systems for targeting, accessing and diagnosing diseased lung compartments. Such compartments could be an entire lobe, a segment, a sub-segment or any such portion of the lung. Diagnosis is achieved in the disclosed embodiments by isolating a lung compartment to obtain various measurements to determine lung functionality. Though COPD is mentioned as an example, the applicability of these methods for treatment and diagnosis is not limited to COPD, but can be applicable to any lung disease.

The methods are minimally invasive in the sense that the required instruments are introduced through the mouth, a tracheostomy, or other site, typically via a bronchoscope, assisted ventilation device, or other non-surgical device passed through the mouth into the trachea and airways. In some embodiments, the patient is allowed to breathe normally during the procedures. Some embodiments may be used with assisted (or positive pressure) ventilation. The methods involve detecting the presence or characteristics (e.g., concentration or pressure) of one or more naturally occurring or introduced gases to determine the presence of collateral ventilation and/or to measure one or more other characteristics of a target lung compartment, such as oxygen saturation of tissue.

Figure 1:
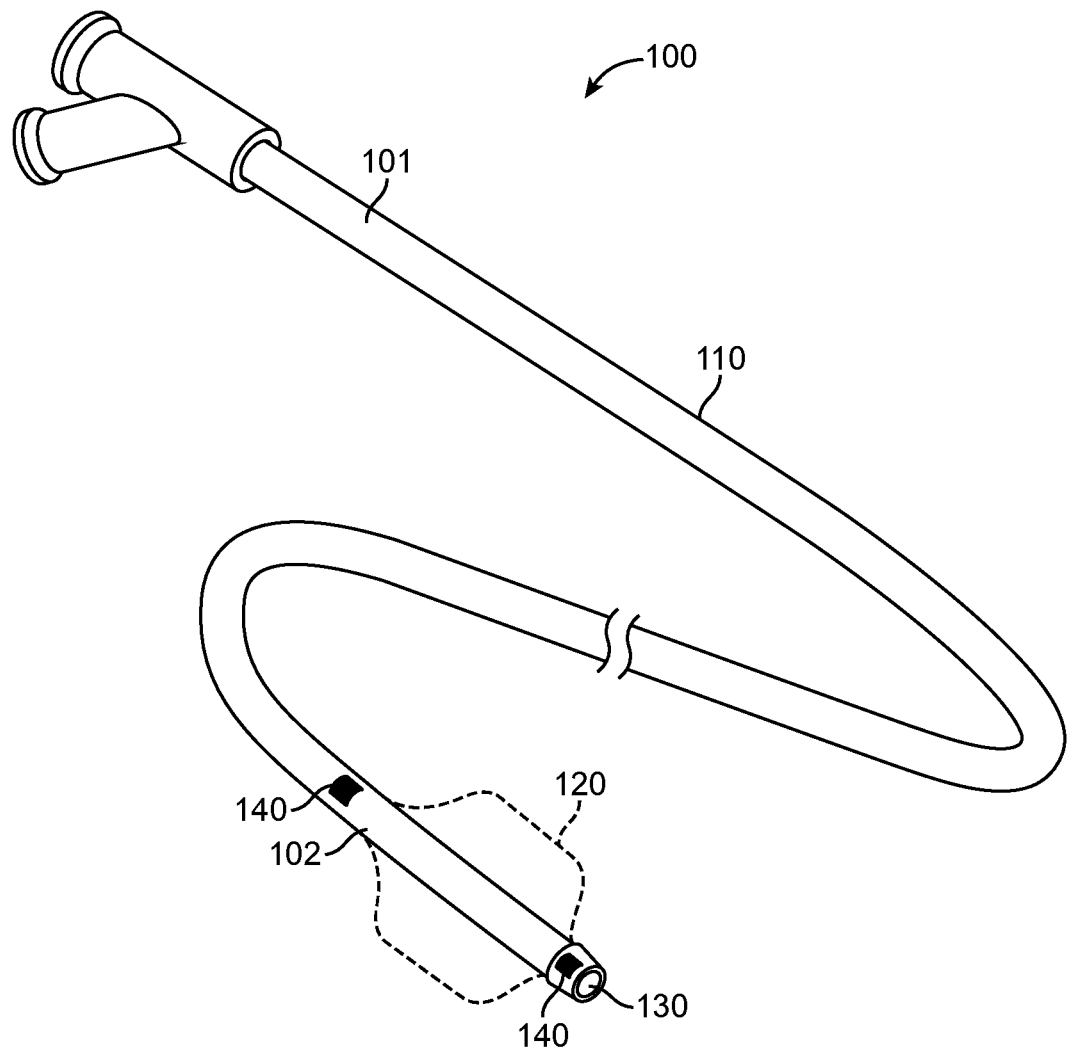
FIG. 1 shows a diagnostic or assessment catheter used in the disclosed methods according to some embodiments of the present invention.
Figure 2:
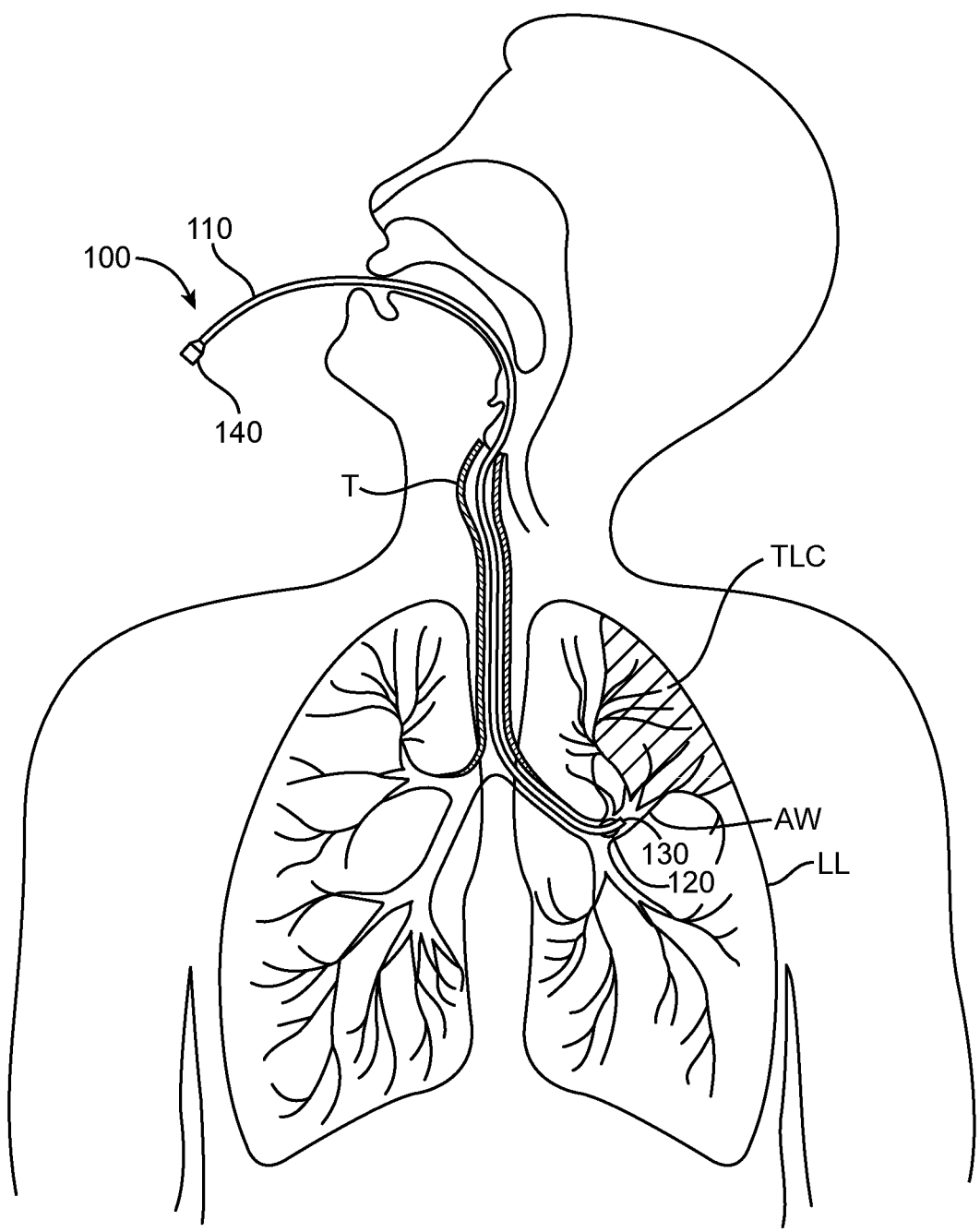
FIG. 2 shows the placement of the catheter shown in FIG. 1 in the lung.

In some of the present embodiments, isolation of the lung comprises sealingly engaging a distal end of a catheter in an airway feeding a lung compartment, as shown in FIGS. 1 and 2. Such a catheter has been disclosed in co-pending published U.S. patent application Ser. No. 10/241,733, which is incorporated herein by reference. As shown in FIG. 1, the catheter 100 comprises a catheter body 110, and an expandable occluding member 120 on the catheter body. The catheter body 110 has a distal end 102, a proximal end 101, and at least one lumen 130, extending from a location at or near the distal end to a location at or near the proximal end.

The proximal end of catheter 100 is configured to be coupled with an external control unit (or "console," not shown), and optionally comprises an inflation port (not shown). The distal end of catheter 100 is adapted to be advanced through a body passageway such as a lung airway. The expandable occluding member 120 is disposed near the distal end of the catheter body and is adapted to be expanded in the airway which feeds the target lung compartment. In one embodiment, the occluding member 120 is a compliant balloon made of transparent material. The transparent material allows visualization using the bronchoscope through the balloon. The occluding member 120 is inflatable via a syringe that is configured to be coupled to the inflation port. Optionally, catheter 100 comprises visual markers at the proximal and distal ends of the balloon to identify the location of the occluding member 120 within the airway prior to inflation. The occluding member 120 material inflates and seals with inflation pressures between 5-20 psi to prevent balloon migration within the airway. This inflation pressure also aids the occluding member 120 in maintaining a symmetrical configuration within the airway, thereby ensuring that the catheter (which is centered within the occluding member 120) will remain centered within the airway. The occluding member 120 material and attachment are also configured to minimize longitudinal movement of the occluding member 120 relative to the catheter body 110 itself. To accommodate the higher inflation pressure, the occluding member 120 is made of a polyurethane such as Pellethane 80A, but can be made of any material that is configured to maintain structural integrity at a high inflation pressure.

Additionally and optionally, catheter 100 further comprises at least one sensor 140 located within or in-line with the lumen 130 for sensing characteristics of various gases in air communicated to and from the lung compartment. The sensors may comprise any suitable sensors or any combination of suitable sensors, and are configured to communicate with control unit 200. Examples of sensors include pressure sensors, temperature sensors, air flow sensors, gas-specific sensors, or other types of sensors. As shown in FIG. 1, the sensors 140 may be located near the distal end 102 of the catheter 100. Alternatively, the sensors 140 may be located at any one or more points along the catheter 100, or in-line with the catheter 100 and within the control unit with one or more measuring components.

As shown in FIG. 2, at least a distal portion of the catheter body 110 is adapted to be advanced into and through the trachea (T). The catheter may optionally be introduced through or over an introducing device such as a bronchoscope. The distal end 102 of the catheter body 110 can then be directed to a lung lobe (LL) to reach an airway (AW) which feeds a target lung compartment (TLC), which is to be assessed. When the occluding member 120 is expanded in the airway, the corresponding compartment is isolated with access to and from the compartment provided through the lumen 130.

Figure 3:
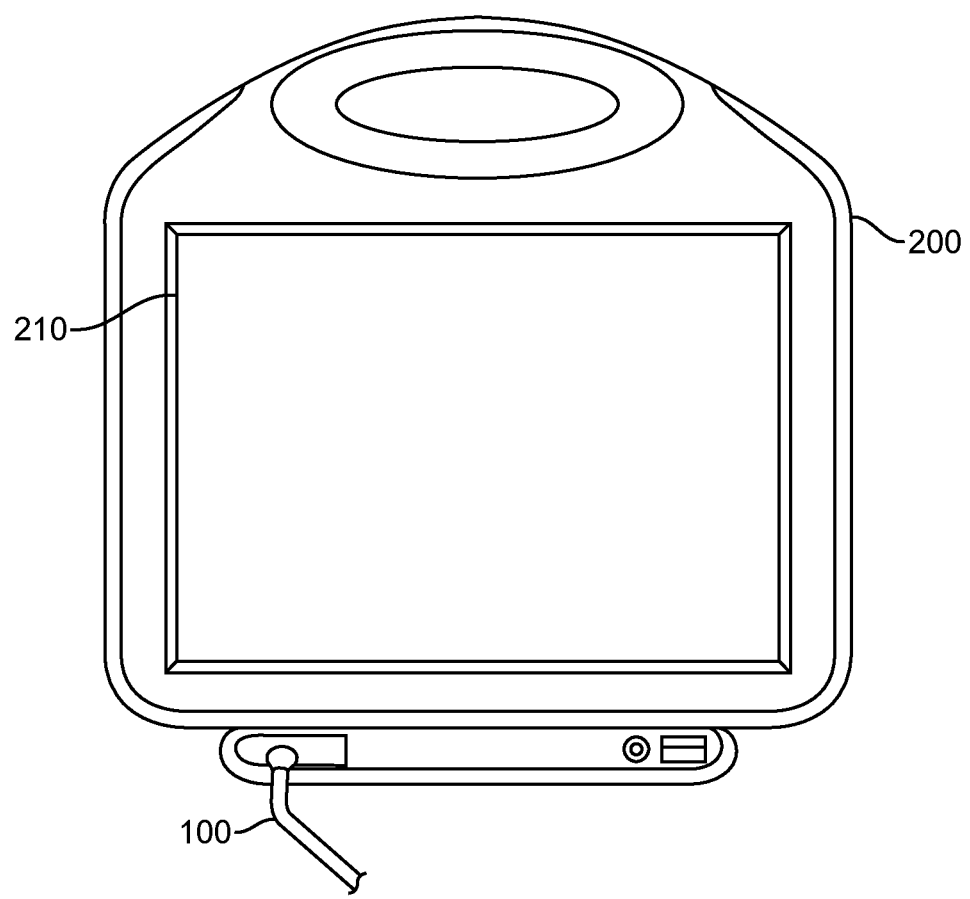
FIG. 3 shows a console configured to receive the catheter shown in FIG. 1.

The proximal end of the catheter 100 is configured to be coupled with a control unit (or "console") 200, as shown in FIG. 3. The control unit 200 comprises one or more measuring components (not shown) to measure lung functionality. The measuring components may take many forms and may perform a variety of functions. For example, the components may include a pulmonary mechanics unit, a physiological testing unit, a gas dilution unit, an imaging unit, a mapping unit, a treatment unit, a pulse oximetry unit or any other suitable unit. The components may be disposed within the control unit 200, or may be attached to the unit 200 from an external source. The control unit 200 comprises an interface for receiving input from a user and a display screen 210. The display-screen 210 will optionally be a touch-sensitive screen, and may display preset values. Optionally, the user will input information into the control unit 200 via a touch-sensitive screen mechanism. Additionally and optionally, the control unit 200 may be associated with external display devices such as printers or chart recorders. At least some of the above system embodiments will be utilized in the methods described below.

CV Assessment in Ventilated Patients. One embodiment includes a method of assessing collateral ventilation in a lung of a patient under an assisted breathing arrangement such as a ventilation mask. In this embodiment, the method involves placing an assisted breathing device, for example the ventilation mask, over the patient's mouth. The catheter 100 is introduced into the lung via a viewing scope, which is in turn introduced into the oral opening of the ventilation mask. Once the catheter has been introduced to the TLC, the TLC is isolated by inflating the occluding member 120. The flow and pressure variations in the isolated lung compartment are then measured while the patient is allowed to breathe under a positive pressure through the ventilation mask. In the absence of collateral channels in a normal lung, expiratory flow from the isolated TLC continuously decreases over several cycles of respiration. In the presence of collateral channels connected to the TLC, there is little or no drop in expiratory flow after isolation of the TLC, which is used to measure the nature and degree of collateral ventilation.

Figure 4:
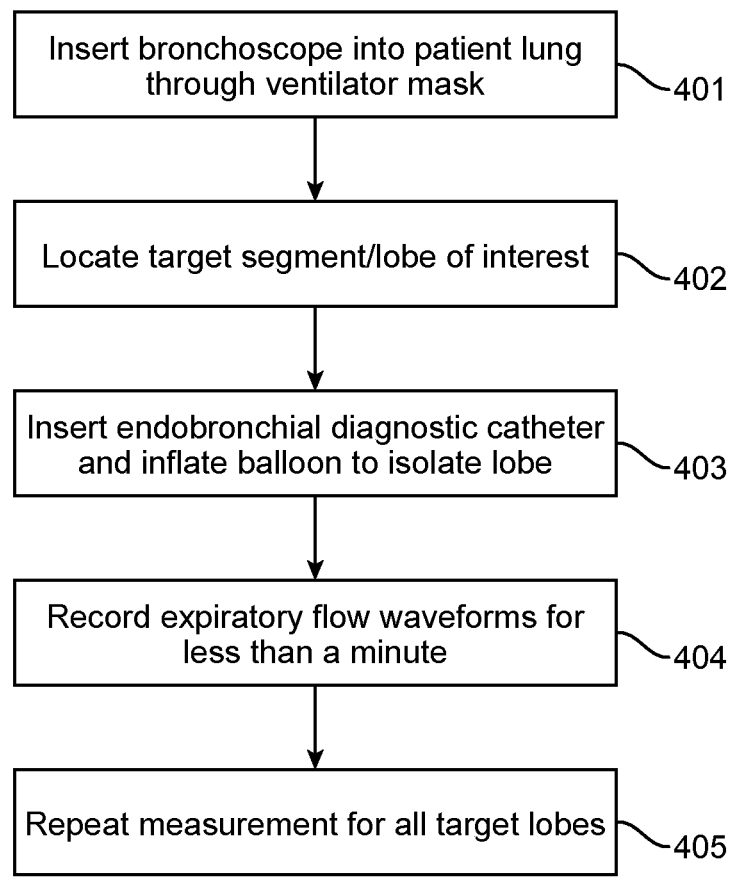
FIG. 4 is a flow diagram illustrating one embodiment of the present invention.

The specific steps involved in this method are shown in greater detail in the flow diagram of FIG. 4. In step 401, a bronchoscope is inserted into a patient lung through the ventilator mask. Thereafter, in step 402, the bronchoscope is used to observe the lung and identify a target segment or lobe of interest. In step 403, the endobronchial diagnostic catheter 100 is inserted into the airway leading to the lung compartment of interest, and the occluding member 120 is inflated to isolate the target lung compartment. Using console 200, the expiratory flow waveforms are then recorded in step 404 for a few cycles of respiration, which may last less than a minute. Thereafter, in step 405, the occlusion balloon is deflated and the diagnostic catheter 100 moved to another lung compartment for another measurement. The procedure may be repeated for several other lung compartments.

Figure 5A:
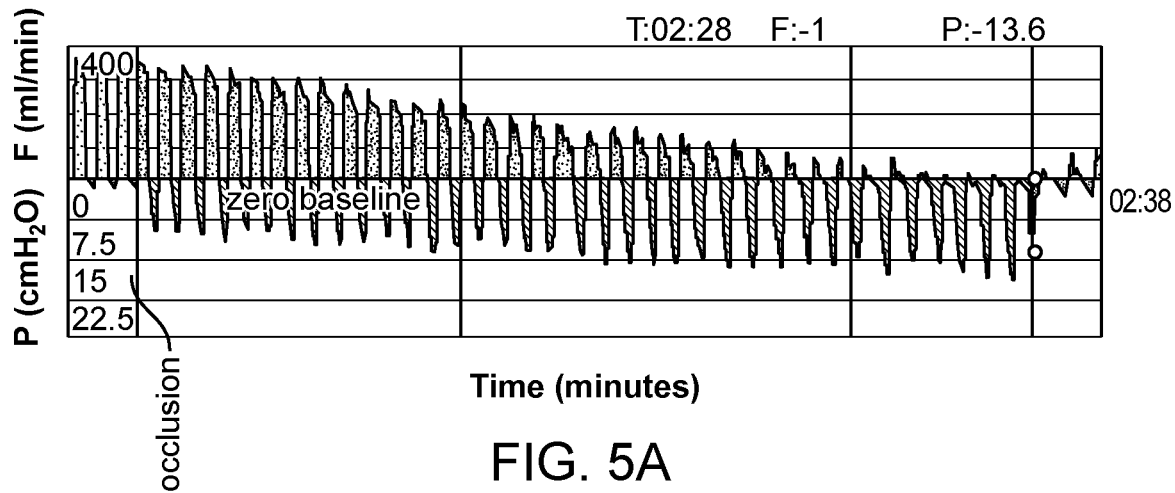
FIGS. 5A-5C show an example of results obtained by using the method illustrated in FIG. 4.
Figure 5B:
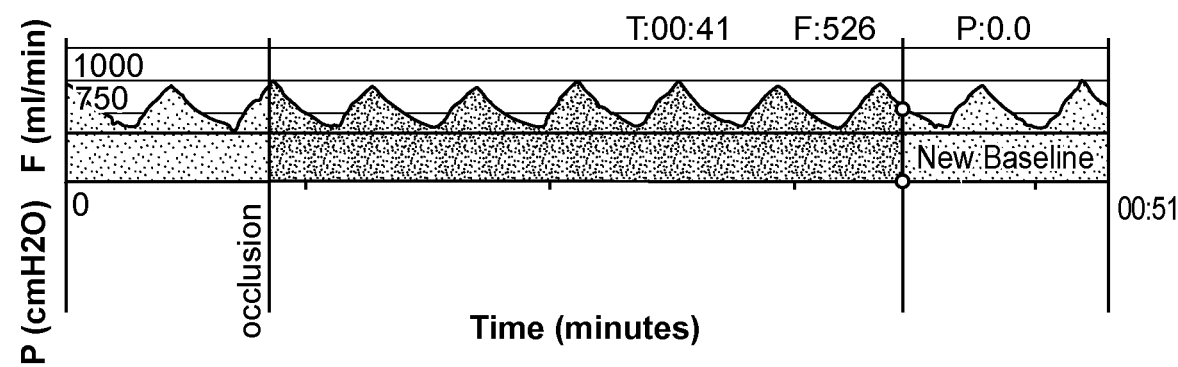
Figure 5C:
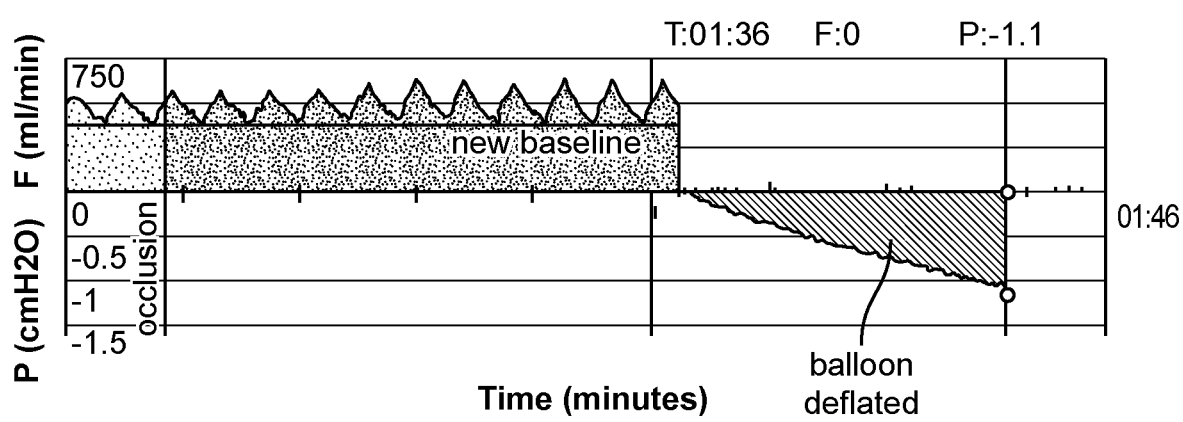

The data is then analyzed to obtain information on the collateral ventilation status of each of the compartments analyzed. Analysis of respiratory waveforms in normal subjects and patients under ventilation is shown in FIGS. 5A-5C. FIG. 5A shows the variation of respiratory flow and pressure over several breath cycles in a normal lung (i.e., one not subject to collateral ventilation) when no ventilator is used. After occlusion, as indicated by the first vertical line, expiratory flow continuously decreases to a baseline that is roughly equal to zero. Further, negative pressure is also detected, and as shown, roughly increases with the duration of the occlusion.

In contrast, FIGS. 5B and 5C show the results of using ventilator-applied positive pressure on a diseased lung segment (i.e., one subject to collateral ventilation). The ventilator creates positive pressure, which is applied relatively uniformly across the lung. This pushes air through adjacent segments/lobes, including through the collateral channels, and ultimately into the catheter 100. As is apparent in FIG. 5B, the net positive pressure does not allow the flow rate to descend to the zero baseline as occurred in FIG. 5A. Instead, a new flow baseline is established. Further, negative pressure, which was apparent in 5A, is not detected until after the occlusion is removed (as shown in FIG. 5C).

Using the above methods, collateral ventilation can be quantified in any of the following ways:
  A. The average expiratory air flow volume versus time can be measured. An increase in volume is indicative of greater collateral ventilation.
  B. The average maximum air flow magnitude can also be measured. An increase in maximum air flow magnitude is indicative of greater collateral ventilation.
  C. An increase in the baseline value for flow could be measured. An increase in baseline flow value is indicative of greater collateral ventilation.
  D. The average change (delta) between flow baseline and the standard zero value could be measured. A greater average change is indicative of greater collateral ventilation.
  E. Alternatively, the physician could decrease or increase the amount of positive pressure during the assessment period. The drop or rise in flow baseline as a result of the change in positive pressure, respectively, may be correlated to the magnitude of collateral ventilation.

In each of the above circumstances, an additional method may optionally be used to normalize flow data recorded from a particular lobe/segment due to differences in lobe/segmental volumes and airway resistances.

The primary advantage of this method is the rapid determination of the presence of collateral flow—often in less than a minute of assessment under ventilation, while other previously known methods require at least 2-5 minutes of measurement. The method also provides for more accurate determination of the degree of collateral ventilation, as a single measurement provides sufficient data to obtain several different parameters relating to collateral flow as detailed above.

Another advantage of this method is that since it applies positive pressure, it may also open hidden collateral channels that are closed due to a layer of secretions. These collateral channels may not be open for study using methods that do not use such positive pressure. Ventilator based assessment may thus forcibly open these occluded channels and provide detection of these hidden collateral pathways.

Method of Assessing Health of a Lobe Using Oxygen Saturation. Another method of improved diagnosis is a method of assessing abnormalities in gas exchange/blood flow within a target lung compartment using the level of oxygen perfusion. Specifically, a TLC is isolated while the overall oxygen saturation of the blood is monitored using a pulse oximeter. A change in the overall oxygen saturation of the blood indicates the level of functioning of the lobe.

Figure 6:
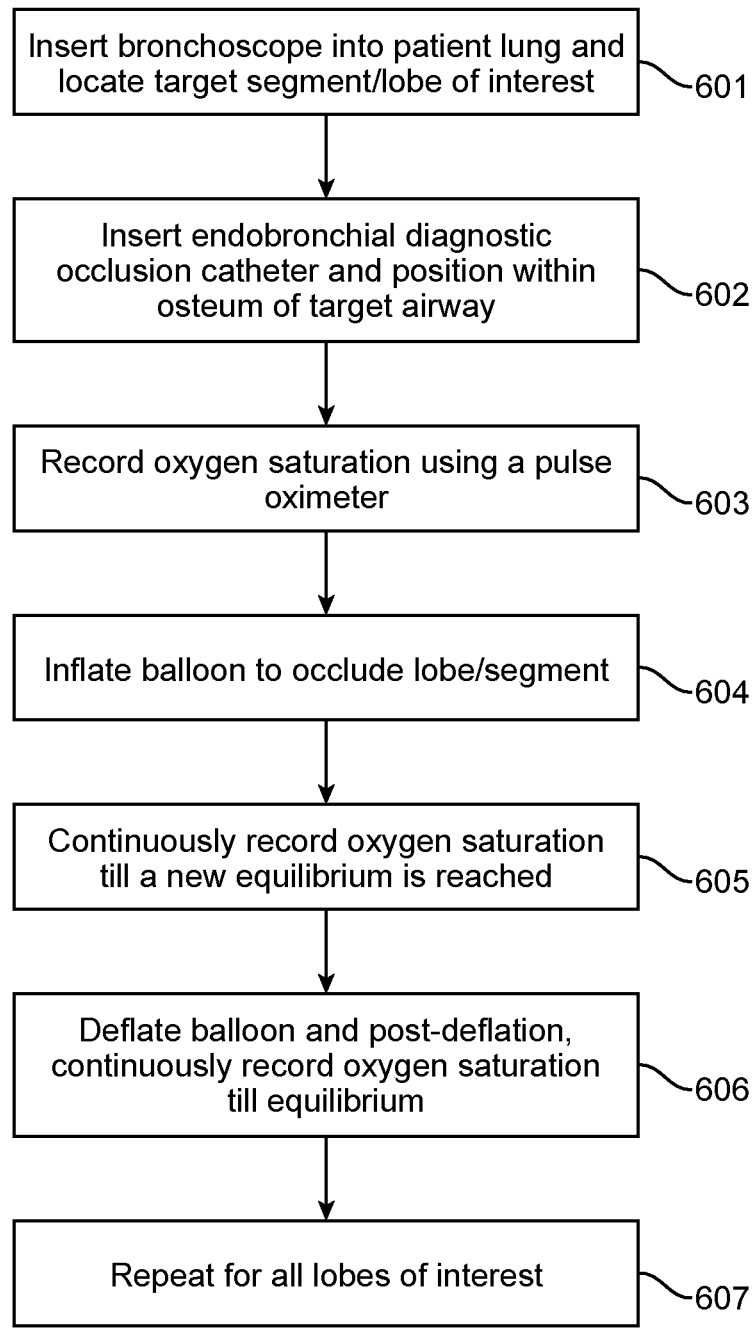
FIG. 6 is a flow diagram illustrating another embodiment of the present invention.

This method is described in further detail in the flow diagram in FIG. 6. As shown in FIG. 6, in the first step 601, a bronchoscope is inserted into a patient's lung and a TLC is identified. Catheter 100 is then introduced in step 602 through the working channel of the bronchoscope and positioned within the airway leading to the TLC. At this location, a pulse oximeter is used to measure oxygen saturation of the tissues in step 603 to provide a baseline value. The TLC is then isolated by inflating the occlusion element (604), and oxygen saturation is continuously recorded by the oximeter until a new equilibrium level is reached (605). The balloon is then deflated and post-deflation, the oxygen saturation is again continuously recorded till the original baseline is reached again (606). The process is repeated for all lobes/segments of interest (607).

The oxygen saturation data may be used in any of several ways to determine the perfusion efficiency of the TLC:
  A. The rate at which oxygen concentration decreases (slope of oxygen saturation versus time) once TLC is isolated is correlated to the percentage the targeted lobe contributes to the overall perfusion of the lung.
  B. The rate at which oxygen concentration increases (slope of oxygen saturation versus time) once the isolation is ceased is correlated to the percentage the targeted lobe contributes to the overall perfusion of the lung.
  C. The difference in oxygen saturation between pre-isolation and post-isolation is also correlated to the percentage the TLC contributes to the overall perfusion of the lung.
  D. Based on the oxygen saturation data received from all lobes, the rate of change in saturation is compared and normalized to adjust for differences in volumes of different lung compartments.
  E. Furthermore, using console 200, flow rate is optionally recorded to quantify ventilation from each lobe. The ventilation data is then optionally used to calculate ventilation and perfusion and potentially determine mismatches between ventilation and perfusion in real-time.

In practice, as the oxygen saturation is constantly in flux based on the degree of sedation, breath rate, position of bronchoscope, secretion status, and other factors, it is important that the above assessment is done fairly quickly to minimize the effects of these other factors on the results. In addition, the oximeter needs to have a sufficiently fine resolution to detect a drop in oxygen saturation due to occlusion. The pulse oximeter may be connected directly to the console 200 for continuous monitoring and recording of oxygen saturation data.

Degree of Oxygen Absorption. In a related embodiment, the degree of oxygen absorption in various lung lobes can be determined in order to determine lung functionality. In this situation, the patient is given supplemental oxygen. The oxygen concentration is then measured in a portion of the bronchial tree where there is no gas exchange (e.g., in a prelobar segment of the bronchus). The oxygen is then measured in various segments downstream of the first measurement. The values are then compared. Segments with poor function will exhibit values similar or closer to the first measurement. Those segments that exhibit values similar or closer to the first measurement (at portion with no gas exchange) are presumed to have decreased functionality.

Method of Assessing the Health of a Lung Compartment Using Flow Ranking. Another method disclosed in the present application is a method of assessing the health of a lung compartment by determining the ability of the compartment to ventilate. A poorly ventilating lobe provides reduced functional benefit to the patient's overall lung function and is thus considered an encumbrance to the rest of the lung. If the target lobe is not ventilating well in comparison to other lobes, the lobe can be isolated via endoscopic lung volume reduction (ELVR) to allow better ventilating lobes to utilize the same space and thereby increase the overall efficiency of the lung.

The method thus involves ranking various segments on the basis of the presence and degree of collateral ventilation within the segment and the segment's ventilation status, as determined by the expiratory and/or inspiratory flow, airway resistance and pressures. The ranking data is then used to determine the course of treatment, which may include placing a one-way valve.

For example, if the target segment ventilates well, then one may not want to isolate the lobe with valves. This may be true even when a segment has no collateral ventilation (CV negative), which would ordinarily have subject it to treatment using an EBV. If such a segment ventilates well, it may still be useful to the functioning of the lung as a whole and a user may choose to not isolate it. Similarly, if a segment has collateral ventilation (CV positive), it would not be indication for treatment with valves. However, if such a segment did not ventilate well, it may indicate that the lobe would benefit from ELVR (e.g., endobronchial valves). ELVR thus becomes a method to divert airflow to lobes with higher perfusion and ventilation rates rather than exclusively a means to reduce lobe size.

Figure 7:
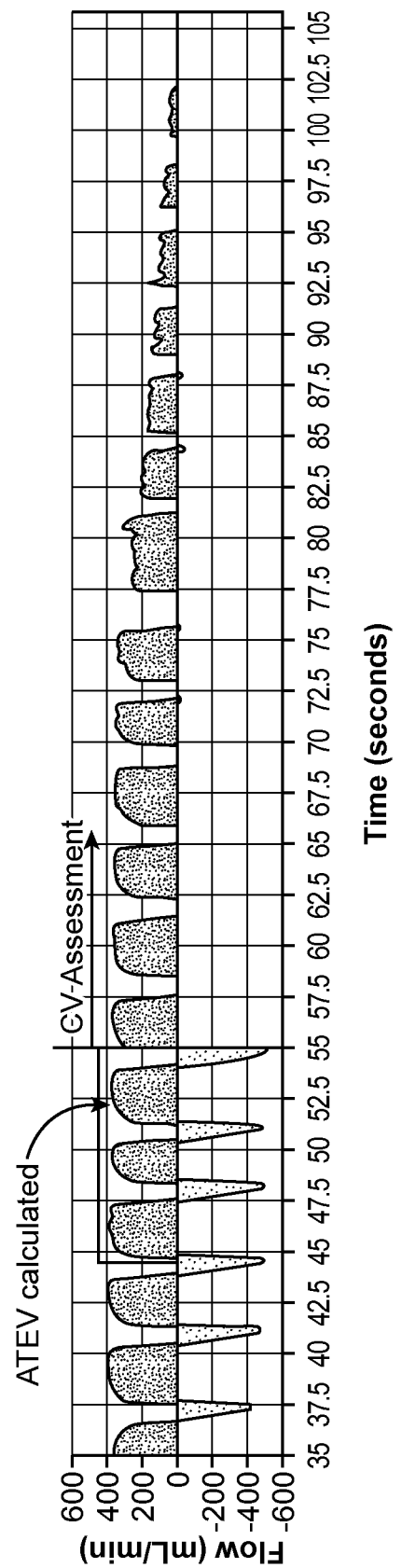
FIG. 7 shows results obtained by using the catheter shown in FIG. 1.

The ventilation status of a lung compartment is measured using the same catheter and method of using a catheter that was shown in FIGS. 1-3. The assessment catheter 100 is introduced into a TLC in a patient. Occluding member 120 is then inflated to isolate the target lung compartment. Characteristics of the air flowing into and out of the TLC are then measured. A result is shown in FIG. 7, where the respiratory flow into and out of the target lung compartment is shown as a function of time. Regular air flow is measured as shown to the left of the line marked "CV assessment". The average tidal flow volume (ATFV) is determined by calculating the average flow rate over the course of a few breath cycles. In this case, the ATFV is determined by looking at the average tidal expiratory volume (ATEV) over the course of three cycles.

Then, when CV assessment begins, the TLC is isolated, resulting in the wave form shown to the left of the line marked "CV assessment". The volume of air expired decreases gradually over time. This indicates an absence of collateral ventilation, since the isolated lung compartment is apparently not receiving inflow even though expiratory flow takes place. The expiratory air flow shown is thus obtained from a normal lung compartment with no collateral ventilation (CV negative).

Figure 9:
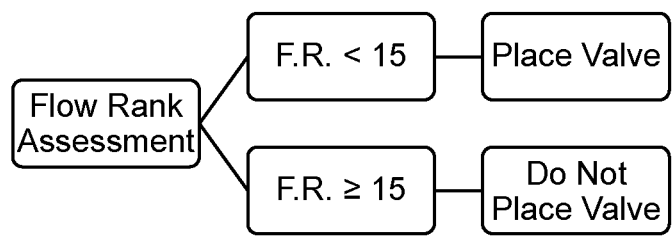
FIG. 9 is a flow diagram illustrating another embodiment of the present invention using the results obtained in FIG. 7.

After sufficient measurements are obtained as shown above, the course of treatment to be followed is determined using a flow ranking parameter and is illustrated in FIG. 9. Flow rank is defined by the relation:

Flow Rank=ATEV (ml)/TLV (liters)*10, where ATEV—is the average tidal flow volume in ml and TLV—the total lung capacity (volume) in liters. Both ATEV and TLV are values obtained from the console 200. The multiplier 10 is added to obtain a convenient numerical value.

Further, if necessary, ATEV may be calculated as follows:

ATEV=TTEV/number of cycles, where TTEV is the total tidal expiratory volume during the given number of cycles.

Both collateral ventilation values and flow rank values for each segment measured are compared to values obtained from the general population, other lobes within the patient, or the same segment within the patient over the course of time. For the purposes of providing an example, a flow rank (FR) value greater than 15 is deemed to indicate a segment that ventilates well, and a FR value less than 5 is deemed to indicate a segment that ventilates poorly.

Figure 8:
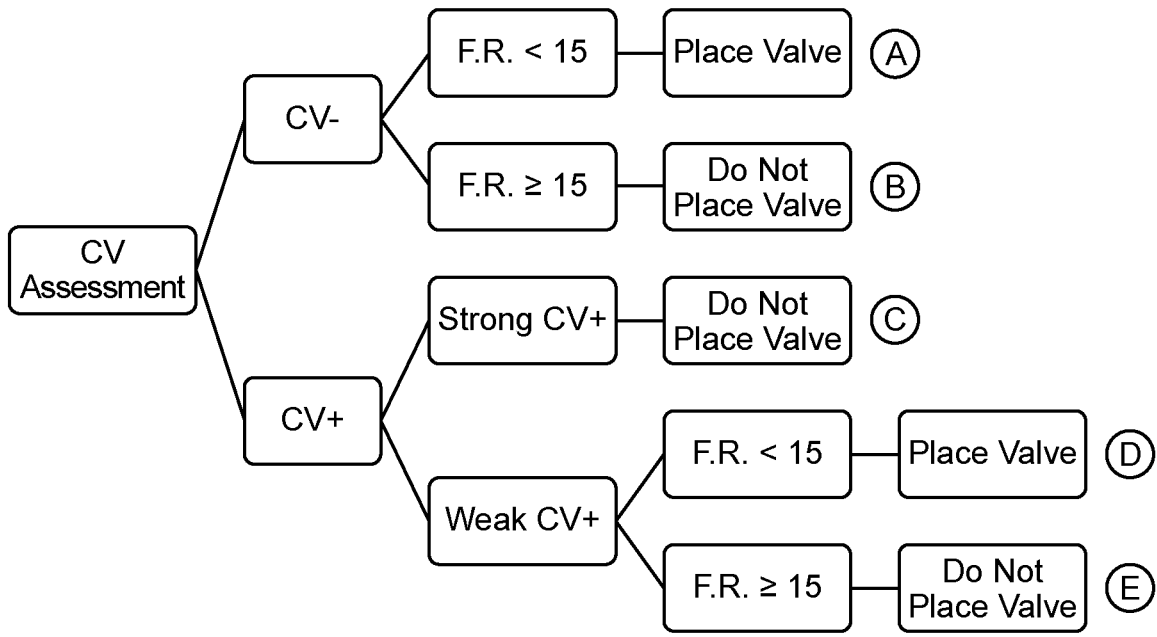
FIG. 8 is a flow diagram illustrating another embodiment of the present invention using the results obtained in FIG. 7.

Using such parameters, a proposed method for determining the course of treatment using both collateral flow characteristics and Flow Ranking is shown in FIG. 8. As shown by option A, when the target lobe does not show collateral ventilation (CV negative), but ventilates less than optimally (FR<15), the lobe is treated by placing a valve. However, as shown in case B, if the lobe is CV− but ventilates very well (FR>15), valve placement is not recommended. If collateral ventilation is strongly present, as in case C, regardless of ventilation status, valve placement is presumed to not significantly influence gas exchange and is not recommended. If, as in case D, a lobe has weak collateral ventilation and does not ventilate well (FR<5), valve placement is recommended, in which case ELVR becomes a method to divert airflow to lobes with higher perfusion and ventilation capabilities, rather than a means to reduce lobe size. If, however, as in case E, the target lobe still shows the ability to ventilate (FR>5), then the lobe is not isolated with valves.

An example of Flow Rank calculation and treatment using the above scheme is shown below, where the average tidal expiratory volume is calculated based on three expiratory cycles. As an example, the values obtained from the graph shown in FIG. 7 are used:

Total Tidal Expiratory Volume (TTEV) over 3 samples (Based on Assessment Displayed in FIG. 7)=42.15 mL and Average Tidal Expiratory Volume (ATEV)=TTEV/3=42.15/3=14.05 mL.

Patient's Total Lung Capacity=5.78 liters.

Flow Rank=ATEV (ml)/TLC (liters)*10= (14.05/5.78)*10=24.3.

Based on the Assessment shown in FIG. 7, Lobe is CV− but F.R. of 24.3>=15.

Valve Placement Not Recommended.

Optionally, treatment options can also be determined without assessment of collateral ventilation, e.g., using Flow Ranking alone, as shown in FIG. 9, in which case the decision to place a valve is based on whether the ventilation status is poor (place valve) or good (do not place valve).

Additionally or optionally, the method of the invention may adopt a baseline flow rate to eliminate patient-to-patient variability. Such as baseline may be obtained by normalizing the flow data with the overall total lung capacity or other lobe/lung volume data. Another solution may be to normalize the values for the target lobes against unaffected or healthy lobes within the same patient to determine the target lobe's proportional output.

Additionally or optionally, other parameters can be measured by console 200 which could also be predictors, such as airway resistance (high tidal resistance=poor ventilating lobe), pressure (low tidal pressure=poor ventilating lobe) and oxygen perfusion efficiency. The inclusion of one or more of the above parameters may provide a better method of ranking overall lobe function (based on resistance, pressure, flow and perfusion) as well as utilizing CV assessment data to guide ELVR therapy decisions.

Clinical Data. The effect of treatments using the five options in FIG. 8 was studied in a clinical setting, and the results are shown in FIGS. 10 and 11. FIG. 10 represents data for patients who received a valve. FIG. 11 represents data for patients who did not receive a valve. The patients in both cases were assessed under three parameters—a) SGRQ (St. George's Respiratory Questionnaire), b) FEV1 (ratio of forced expiratory volume in 1 second to forced vital capacity), and c) 6MWT (6 minute walk test). The change between baseline (pre valve-placement) and post-30 day follow up values were determined in patients treated using the several options.

Some results for patients implanted with a valve are shown in FIG. 10. The chart reflects data collected for patients:
  Who Received Emphasys Valves;
  With Atelectasis of the Target Lobe;
  For Whom the Collateral Ventilation Assessment Measured CV-negative;
  For Whom the Flow Rank with Collateral Ventilation Assessment diagnostic algorithm recommends a valve; and
  For Whom the Flow Rank without CV assessment recommends a valve.

Some results for patients implanted with a valve are shown in FIG. 11. The chart reflects data collected for patients:
  With no Atelectasis in Target Lobe; For Whom Collateral Ventilation Assessment Measured CV-positive in Target Lobe;
  For Whom the Flow Rank with Collateral Ventilation Assessment diagnostic algorithm does not recommend a valve; and
  For Whom the Flow Rank without CV assessment does not recommend a valve.

As observed in FIGS. 10 and 11, among all the methods of screening patients, Flow Ranking both with and without CV assessment appears to identify those patients who would benefit from ELVR therapy most optimally, as the positive values of test parameters are highest for these two categories of patients.

The flow ranking measurement and algorithm potentially opens treatment options to both heterogeneous and homogeneous emphysema patients and offers an opportunity to screen homogeneous emphysema patients with low flow rank.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. A method of assessing the functionality of a lung segment in a patient, the method comprising:
  introducing a diagnostic catheter into the lung segment, wherein the diagnostic catheter comprises a distal end comprising an occluding member and a proximal end configured to be attached to a console;
  inflating the occluding member to isolate the lung segment;
  monitoring blood oxygen saturation of the patient; and
  determining functionality of the lung segment based on a rate of change of blood oxygen concentration.

2. The method of claim 1, wherein the monitoring step comprises monitoring oxygen saturation before and after the inflating step.

3. The method of claim 1, further comprising deflating the occluding member after the monitoring step.

4. The method of claim 3, further comprising monitoring oxygen saturation after the deflating step.

5. The method of claim 1, wherein the monitoring step is conducted by a pulse oximeter.

* * * * *